United States Patent [19]

Van De Puy et al.

[11] 4,334,099
[45] Jun. 8, 1982

[54] PREPARATION OF HEXAFLUOROACETONE FROM HEXAFLUOROTHIOACETONE DIMER

[75] Inventors: Michael Van De Puy, Cheektowaga; Louis G. Anello, Hamburg; Martin A. Robinson, East Amherst, all of N.Y.

[73] Assignee: Allied Corporation, Morris Township, Morris County, N.J.

[21] Appl. No.: 217,943

[22] Filed: Dec. 18, 1980

[51] Int. Cl.³ ............................................... C07C 45/56
[52] U.S. Cl. ................................ 568/386; 260/544 F
[58] Field of Search ................ 568/386, 407, 399, 400

[56] References Cited

U.S. PATENT DOCUMENTS 3,006,973 10/1961 Hauptschein et al. .............. 568/407
3,257,457  6/1966 Anello et al. ....................... 568/394
3,367,971  2/1968 Madison ............................. 568/407
3,391,119  7/1968 Anderson ........................... 568/386
4,057,584 11/1977 Touzuka et al. .................... 508/399

OTHER PUBLICATIONS

Middleton et al., J. Org. Chem., vol. 30, pp. 1384-1390 (1965).
Martin, J. Chem. Soc., pp. 2944-2947 (1964).
Kitazume et al., Chem. Letters, pp. 267-271 (1973).

Primary Examiner—Natalie Trousof
Assistant Examiner—James H. Reamer
Attorney, Agent, or Firm—Thomas D. Hoffman

[57] ABSTRACT

The production of hexafluoroacetone by liquid phase reaction, at elevated temperatures, from hexafluorothioacetone dimer in an aprotic solvent containing an effective amount of an alkali metal fluoride with at least about a stoichiometric amount of an oxidizing agent selected from the group consisting of HgO, Ag$_2$O, Cu$_2$O, CuO, P$_2$O$_5$, MIO$_3$ and MIO$_4$ wherein M is an alkali metal or alkaline earth metal. HgO and MIO$_3$ are the preferred oxidizing agents; KIO$_3$ is most preferred.

8 Claims, No Drawings

PREPARATION OF HEXAFLUOROACETONE FROM HEXAFLUOROTHIOACETONE DIMER

DESCRIPTION

BACKGROUND OF THE INVENTION

This invention relates to the one-step preparation of hexafluoroacetone by liquid phase reaction of hexafluorothioacetone dimer in an aprotic solvent containing alkali metal fluoride, at elevated temperature, with selected metallic and non-metallic oxides.

Hexafluoroacetone is a known compound useful as an intermediate in the preparation of hexafluoroisobutylene and hexafluoroisopropanol. Hexafluoroacetone also forms terpolymers with tetrafluoroethylene and with ethylene.

The preparation of hexafluorothioacetone dimer [2,2,4,4-tetrakis(trifluoromethyl)-1,3-dithietane] is disclosed by K. V. Martin in *J. Chem. Soc.*, 2944 (1964). A mixture of hexafluorothioacetone dimer and hexafluorothioacetone monomer is produced by reacting hexafluoropropene with sulfur vapor over a carbon catalyst at 425° C.; in the presence of a catalyst such as dimethylformamide, the monomer is converted into hexafluorothioacetone dimer.

In the presence of fluoride ion, a solution of hexafluorothioacetone dimer in dimethylformamide at ambient temperature is partially dissociated to produce an equilibrium mixture of monomeric and dimeric hexafluorothioacetone (T. Kitazume et al., *Chemistry Letters*, 267 (1973)).

The preparation of hexafluoroacetone by the gas phase oxidation of hexafluorothioacetone dimer with nitric oxide or sulfur dioxide in a Vycor tube packed with quartz heated to at 650° C. is disclosed by W. J. Middleton and W. H. Sharkey in *J. Org. Chem*, Vol. 30, pages 1384–1390 (1965).

Hexafluoroacetone is also prepared (1) by high temperature gas phase fluorination of hexachloroacetone with HF in the presence of a chromium catalyst (L. G. Anello et al. in U.S. Pat. No. 3,257,457) and (2) by gas phase oxidation of hexafluoropropene with $O_2$ in the presence of a fluorinated alumina catalyst (T. Touzuka et al. in U.S. Pat. No. 4,057,584).

These prior art preparations of hexafluoroacetone are effected in the gas phase with corrosive reactants such as HF over specially prepared catalysts such as chromium or fluorinated alumina or over quartz heated to 650° C.

It is an object of the present invention to provide a process for liquid phase preparation of hexafluoroacetone from hexafluorothioacetone dimer. This and other objects and advantages will be apparent from the disclosure which follows.

SUMMARY OF THE INVENTION

In accordance with the present invention there is provided a process for preparation of hexafluoroacetone, which comprises reacting, at elevated temperatures in the liquid phase, hexafluorothioacetone dimer in an aprotic solvent containing an effective amount of an alkali metal fluoride with at least about a stoichiometric amount of an oxidizing agent selected from the group consisting of HgO, Ag$_2$O, Cu$_2$O, CuO, P$_2$O$_5$, MIO$_3$ and MIO$_4$ wherein M is an alkali metal or alkaline earth metal.

DETAILED DESCRIPTION OF THE INVENTION

The present invention provides a one step liquid phase reaction for the preparation of hexafluoroacetone by dissolving hexafluorothioacetone dimer in a suitable aprotic solvent, preferably having less than about 0.05% by weight water and containing an effective amount of an alkali metal fluoride with at least about a stoichiometric amount of a selected metallic or nonmetallic oxidizing agent. The hexafluorothioacetone monomer generated by the action of an effective amount of a alkali metal fluoride on hexafluorothioacetone dimer in a suitable aprotic solvent is attacked by the selected metallic and nonmetallic oxidizing agents while the heterogeneous reaction mixture is heated at elevated temperatures for a time sufficient to convert hexafluorothioacetone dimer into hexafluorothioacetone for oxidation to hexafluoroacetone.

Among the aprotic solvents found useful in the present invention are dimethylformamide, dimethylacetamide, dimethyl sulfoxide, acetonitrile, N-methyl pyrrolidone, and the macrocyclic polyethers commonly called crown ethers. Dimethylformamide is the preferred aprotic solvent. Since hexafluoroacetone very readily forms a hydrate (mp 49° C.), the aprotic solvent and other reagents, such as starting material, hexafluorothioacetone dimer, as well as the reactor, should preferably be dry in order to obtain a good yield of hexafluoroacetone, essentially free of the corresponding hydrate. Specifically, the total reactor including all reactants and the aprotic solvent should preferably be dry, i.e., total water content should be no more than about 0.05% by weight of water.

The alkali metal fluoride found useful in the generation of hexafluorothioacetone monomer from hexafluorothioacetone dimer in an aprotic solvent such as dimethylformamide includes LiF, NaF, and KF. Since KF is more soluble in dimethylformamide, KF is the preferred alkali metal fluoride. The effective amount of alkali metal fluoride varies with the water content of the reaction mixture. When the water content in the reaction mixture, and specifically the aprotic solvent, preferably DMF, is maintained at the preferred value of no more than about 0.05 weight % of water, the effective amount of the preferred KF is between about 1 and 5 weight % KF per weight of hexafluorothioacetone dimer. An upper limit on the effective amount of alkali metal fluoride, preferably KF, is not critical; an amount of alkali metal fluoride, preferably KF, in excess of 1 weight % per weight of hexafluorothioacetone is effective. When the water content of the reaction mixture, specifically of the aprotic solvent, is maintained at no more than about 0.05 weight %, only economic considerations would preclude employing an effective amount of alkali metal fluoride, preferably KF, in excess of 5 weight % of the hexafluorothioacetone dimer.

While the prior art preparations required high temperature gas phase reaction conditions, surprisingly it was discovered that the metallic and non-metallic oxide oxidizing agents selected from the group consisting of HgO, Ag$_2$O, Cu$_2$O, CuO, P$_2$O$_5$, MIO$_3$ and MIO$_4$ wherein M is an alkali metal or alkaline earth metal allowed one step conversion of hexafluorothioacetone generated by dissolving hexafluorothioacetone dimer in an aprotic solvent such as dimethylformamide in the presence of alkali metal fluoride into hexafluoroacetone. The preferred oxidizing agents are HgO and $MIO_3$ wherein M is an alkali metal or alkaline earth metal. Both HgO and $MIO_3$ produce hexafluoroacetone in high yield, uncontaminated by side products such as $(CF_3)_3CH$ or $CF_3$-COF. Due to the environmental problems associated with mercuric salts, $MIO_3$ is more preferred. For economic reasons, $KIO_3$ is most preferred.

The $(CF_3)_3CH$ side product produced in addition to the desired hexafluoroacetone when the oxidizing agent is $P_2O_5$, $Cu_2O$ or CuO, is conveniently separated from hexafluoroacetone by any standard technique such as fractional distillation. However, the presence of $(CF_3)_3CH$ is unlikely to adversely affect many reactions intended for hexafluoroacetone, such as reduction thereof to hexafluoroisopropanol, and the separation of $(CF_3)_3CH$ is conveniently delayed until the total reaction sequence is completed.

While the stoichiometric amount of oxidizing agent required to convert hexafluorothioacetone dimer into hexafluoroacetone varies with the oxidizing agent selected, the stoichiometric amount of oxidizing agent found effective was in the range of about 2 moles, i.e. 1.80-2.00 moles to about 5.0 moles of oxidizing agent per mole of hexafluorothioacetone dimer. Generally, the stoichiometric amount of oxidizing agent in excess of about 2 moles, preferably about 2.5 moles, of anhydrous $KIO_3$ of oxidizing agent to one mole of hexafluorothioacetone dimer was found effective. Only economic considerations would preclude employing an amount of oxidizing agent in excess of 5.0 moles per one mole of hexafluorothioacetone dimer.

For a preferred embodiment of the present invention, anhydrous hexafluorothioacetone dimer in dimethylformamide and containing anhydrous KF was agitated with anhydrous $KIO_3$. The heterogeneous reaction mixture was heated until the dimer refluxed and the temperature of the stirred reaction mixture was slowly raised to the boiling point of dimethylformamide. The hexafluoroacetone (bp $-28°$ C.) was condensed under sufficiently high pressures and low temperature. Further purification can conveniently be effected by fractional distillation.

Exact contact times and reaction temperatures are not critical; a suitable minimum temperature is about 60° C. (under reaction pressure) and a suitable maximum temperature is about 150° to 175° C., conveniently about 150° C. for most inorganic reactants. Contact times are conveniently from about 2 hrs. to 6 hrs.; longer contact times result in higher conversion for hexafluorothioacetone dimer.

The present invention can conveniently be operated under continuous or batch conditions.

The invention will be further illustrated and described by the following examples, the details of which should not be construed as limiting the invention except as may be required by the appended claims.

EXAMPLE 1

A 500-mL three-necked flask was fitted with a mechanical stirrer, thermometer, and a water-cooled condenser. The outlet of the condenser was attached to a $-78°$ C. cold trap. Under an atmosphere of nitrogen, the flask was charged with 1 g anhydrous KF, 30 g $KIO_3$, 20.0 g hexafluorothioacetone dimer (recrystallized), and 100 mL dry dimethylformamide (water content 0.004%) freshly distilled from $P_2O_5$. The flask was immersed in a bath at 70° C. The color of the reaction mixture turned light brown after a few minutes. The mixture was then heated to 140° C. over 20 minutes. The temperature rose gradually to 149° C. during an additional 100 minutes. The mixture turned dark brown as elemental iodine was formed. In the cold trap 16.3 g hexafluoroacetone (HFA) (95% by GC and IR) was collected. The yield was 89%.

EXAMPLES 2-7

The following examples were run as described in Example 1 except the oxidizing agent (oxidant) and weight of reactants were varied as summarized in Table I.

TABLE I

| Example | 1 | 2 | 3 | 4 |
|---|---|---|---|---|
| Oxidant | $KIO_3$ | HgO | $Ag_2O$ | $P_2O_5$ |
| Wgt. (g) | 30 | 62.4 | 34.2 | 16.0 |
| (mol) | (.140) | (.288) | (.148) | (.113) |
| HFTA Dimer (g)[1] | 20.0 | 26.0 | 14.0 | 22.1 |
| (Purity) | (100%) | (91%) | (86%) | (100%) |
| Mol | .055 | .065 | .033 | .061 |
| Oxidant: HFTA Dimer (mol) | 2.55 | 4.45 | 4.50 | 1.86 |
| KF (g) | 1.0 | 5.2 | 6.0 | 4.7 |
| $DMF^2$ (mL) | 100 | 150[a] | 80 | 150 |
| Reaction Time (hrs.) | 2[b] | 5[c] | 6[d] | 1¼[e] |
| Wgt. of Crude Product (g) | 16.3 | 12.8 | 12.0 | 10.2 |
| Products[3] | 95% HFA | 98% HFA | 80% HFA | 61% HFA[i] |
| % of Crude Product | | | 20% $CF_3COF$ | 30% $(CF_3)_3CH^j$ |
| Yield of HFA[4] | 89% | 62% | 88% | 31% |

| Example | 5 | 6 | 7 |
|---|---|---|---|
| Oxidant | $NaIO_4$ | $Cu_2O$ | CuO |
| Wgt. | 21.4 | 20.0 | 20.0 |
| (mol) | (.100) | (.140) | (.251) |
| HFTA Dimer (g)[1] | 20.0 | 26.0 | 26.0 |
| (Purity) | (95%) | (91%) | (91%) |
| Mol | .052 | .065 | .065 |
| Oxidant: HTFA Dimer (mol) | 1.93 | 2.16 | 3.87 |
| KF (g) | 1.0 | 5.0 | 1.0 |
| $DMF^2$ (mL) | 100 | 125 | 125 |
| Reaction Time (hrs.) | 4¼[f] | 2⅜[g] | 2⅜[h] |
| Wgt. of Crude Product (g) | 10.5 | 10.3 | 7.9 |
| Products[3] % of Crude Product | 85% HFA[i] | 64% HFA[i] 30% $(CF_3)_3CH^j$ | 70% HFA[i] 21% $(CF_3)_3CH^j$ |
| Yield of HFA[4] | 52% | 31% | 26% |

NOTES FOR TABLE I
[1] HFTA Dimer is hexafluorothioacetone dimer
[2] DMF is dimethylformamide
[3] Analysis by gas chromatography and I.R.
[4] HFA is hexafluoroacetone
[a] Water content was 0.02% by weight
[b] See Example 1 for details
[c] Reaction temperature was from 25° to 140°; HgS first appeared at 63° C., HFA collected in cold trap at 120° C.
[d] Reaction temperature was 110° to 140° C.
[e] Reaction temperature was 30° to 150° C.; at 120° C. the color of reaction mixture was yellow
[f] Reaction temperature was 118° to 152° C.; at 120° C. the color of reaction mixture was brown and HFA first appeared in cold trap
[g] Reaction temperature was 73° to 150°; at 73° C. color of reaction mixture was red; at 146° C. liquid first appeared in trap
[h] Reaction temperature was 120° to 150° C.; at 135° C. liquid first appears
[i] The balance was not identified
[j] $(CF_3)_3CH$ was identified by IR, 1H and 19F - NMR

We claim:
1. A process for preparation of hexafluoroacetone, which comprises reacting, at elevated temperatures, in the liquid phase, hexafluorothioacetone dimer in an aprotic solvent containing an effective amount of an alkali metal fluoride with at least about a stoichiometric amount of an oxidizing agent selected from the group consisting of HgO, $Ag_2O$, $Cu_2O$, CuO, $P_2O_5$, $MIO_3$ and $MIO_4$ wherein M is an alkali metal or alkaline earth metal.

2. The process of claim 1 wherein the oxidizing agent is HgO.

3. The process of claim 1 wherein the oxidizing agent is $MIO_3$.

4. The process of claim 3 wherein the oxidizing agent is $KIO_3$.

5. The process of claim 1, 2 or 4 wherein the aprotic solvent is dimethylformamide and the alkali metal fluoride is KF.

6. The process of claim 5 wherein the dimethylformamide contains no more than about 0.05 weight % water and the effective amount of KF is between about 1 and 5 weight % of the weight of hexafluorothioacetone dimer.

7. The process of claim 5 wherein the reaction is agitated.

8. The process of claim 7 wherein the total water content is no more than about 0.05% by weight.

* * * * *